US00PP30038P2

(12) United States Plant Patent
Egger

(10) Patent No.: US PP30,038 P2
(45) Date of Patent: Dec. 25, 2018

(54) ***PENSTEMON* PLANT NAMED 'RASPBERRY TAFFY'**

(50) Latin Name: ***Penstemon* hybrid**
Varietal Denomination: Raspberry Taffy

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,858

(22) Filed: Aug. 15, 2017

(51) Int. Cl.
*A01H 5/02* (2018.01)

(52) U.S. Cl.
USPC ..... Plt./465

(58) Field of Classification Search
USPC ..... Plt./263.1, 465
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct cultivar of *Penstemon* plant characterized by medium large size raspberry red flowers in good size inflorescences, long bloom time, upright, medium plant size, and excellent vigor.

1 Drawing Sheet

Botanical denomination: *Penstemon* hybrid.
Variety designation: 'Raspberry Taffy'.

BACKGROUND OF THE INVENTION

The present invention relates to a new and distinct cultivar of *Penstemon*, given the name, 'Raspberry Taffy'. *Penstemon* is in the family Plantaginaceae (formerly Scrophulariaceae). This plant originated as an open pollinated seedling out of *Penstemon* 'Boysenberry Taffy' in the display garden at the nursery in Canby, Oreg. This new cultivar was selected for its upright growing habit and medium large red flowers. It is a good fit for the nursery's "Taffy" series of *Penstemon.*

Compared to plants of *Penstemon* 'Cha Cha Cherry', U.S. Plant Pat. No. 28,163, the new cultivar is taller with larger, more raspberry red than red flowers, and has greener calyces, seed heads, and stems.

Compared to *Penstemon* 'Boysenberry Taffy', U.S. Plant Pat. No. 25,361, the new cultivar has redder toned flowers instead of purple toned flowers.

*Penstemon* 'Raspberry Taffy' is uniquely distinguished by its:

1. medium large size raspberry red flowers in good size inflorescences,
2. long bloom time,
3. upright, medium plant size, and
4. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the habit of a group of eighteen-month-old plants in late June in Canby, Oreg.

FIG. 2 shows a close up of the inflorescence.

DETAILED PLANT DESCRIPTION

The following is a detailed description of the new *Penstemon* cultivar based on observations of eighteen-month-old specimens grown outside in the comparison garden in full sun in Canby, Oreg. in late June. The color descriptions are all based on The *Royal Horticultural Society Colour Chart,* 5$^{th}$ edition, 2007.

Plant:

*Type.*—Herbaceous perennial.
*Form.*—Upright, branching.
*Cold hardiness.*—USDA Zone 7-10.
*Size.*—Grows to 43 cm wide and 74 cm high to top of inflorescence.
*Vigor.*—Excellent.
*Stem number.*—About 9 main stems from the crown.
*Stem.*—Upright, to about 44 cm long and 5 mm wide, glabrous at base to glandular pubescent toward rachis, internodes grow to 4.5 cm long, Yellow Green 145B tinted Greyed Purple 187C in sun.
*Rooting.*—Roots easily from stem cuttings.

Leaf:

*Type.*—Simple.
*Arrangement.*—Opposite.
*Shape.*—Lanceolate.
*Venation.*—Pinnate, main vein on top Yellow Green 145B, bottom side Yellow Green 145C.
*Margins.*—Entire.
*Apex.*—Acuminate.
*Base.*—Rounded.

*Blade size*.—Grows to 8 cm long and 2 cm wide.

*Surface texture*.—Glabrous on both sides.

*Petiole*.—None, sessile.

*Leaf color*.—Topside Green 137B, bottom side closest to Yellow Green 147B.

Inflorescence:

*Type*.—Terminal, many flowered, dense thyrse.

*Number of flowers per inflorescence*.—24 to 56.

*Size of inflorescence*.—Grows to 33 cm long and 12 cm wide.

*Peduncle*.—Grows to 5 cm long and 3 mm wide, pubescent, Yellow Green 145B tinted Greyed Purple 187C in sun.

*Rachis*.—13 cm to 31 cm long and 4 mm wide, pubescent, Yellow Green 145B tinted Greyed Purple 187C in sun.

*Pedicel*.—Grows to 15 mm long and 1 mm wide, somewhat weak in strength, pubescent, Greyed Purple 187B.

*Bloom period*.—Mid-June to frost in October in Canby, Oreg. if spent flowers are removed.

Flower bud:

*Size*.—2.4 cm long and to 8 mm wide.

*Description*.—Closed tubular, bulging, flattened ventrically.

*Color*.—Red Purple 59B.

Flower:

*Type*.—Zygomorphic, perfect.

*Shape*.—Tubular, bilabiate.

*Size*.—Grows to 4 cm to 4.5 cm long and 3.5 cm to 4 cm wide.

*Corolla description*.—Grows to about 4.5 cm long and 3.5 cm wide; tube is bulbous in the calyx for 5 mm long and 4 mm wide, narrowing then widening for 25 mm and flaring to 17 mm wide, 5 lobes, the two smaller top lobes flare back (each 12 mm wide and to 14 mm deep) and two larger lateral lobes curl back slightly (11 mm wide and 13 mm deep), and the lower lobe flares curls back (10 mm wide and 11 mm deep), lobes overlap slightly, lobe margins entire, tips obtuse; outside glandular pubescent, inside glabrous; outside color Red Purple 59B, inside color lobes Red Purple 58B, tube White N155A with bee tracks and band below lobes Greyed Purple 187B.

*Calyx description*.—9 mm deep and 9 mm wide, 5 overlapping lobes cut to the base, each lobe broadly obovate in shape, 8 mm long and 8 mm wide, margins entire, tip acute, base cuneate, outside Yellow Green 147B tinted Greyed Purple 187A where in sun, inside Yellow Green 147B, glabrous inside and glandular pubescent outside.

*Pistil description*.—1, 28 mm long, ovary 6 mm long and 3.5 mm wide, Yellow Green 148C; style 22 mm long and less than 1 mm wide, style Greyed Purple 187C on lower ¾ blending to White N155B, stigma White NN155C.

*Stamen description*.—5, White NN155B, one sterile without an anther, held within the corolla, grows to 27 mm long and less than 1 mm wide, filaments 25 mm long and less than 1 mm wide, anthers 3 mm long and 3 mm wide, Purple N77B, pollen White NN155C.

*Fragrance*.—None.

*Lastingness*.—A flower lasts 5 to 6 days.

Fruit:

*Type*.—Capsule.

*Fertility*.—Fair.

*Size*.—11 mm deep and 11 mm wide.

*Shape*.—Conical.

*Color*.—Brown 200A.

Seed:

*Shape*.—Irregular.

*Size*.—2 mm long.

*Color*.—Brown 200A.

Pests and diseases: The new cultivar is typical to the genus. No problems have been found in Canby, Oreg.

I claim:

1. A new and distinct cultivar of *Penstemon* plant substantially as illustrated and described.

* * * * *

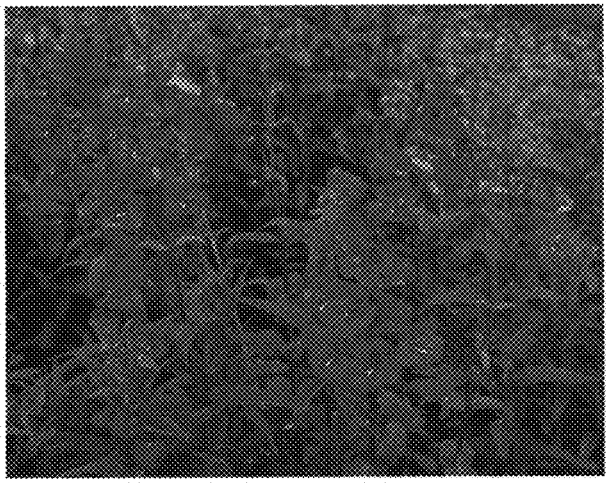

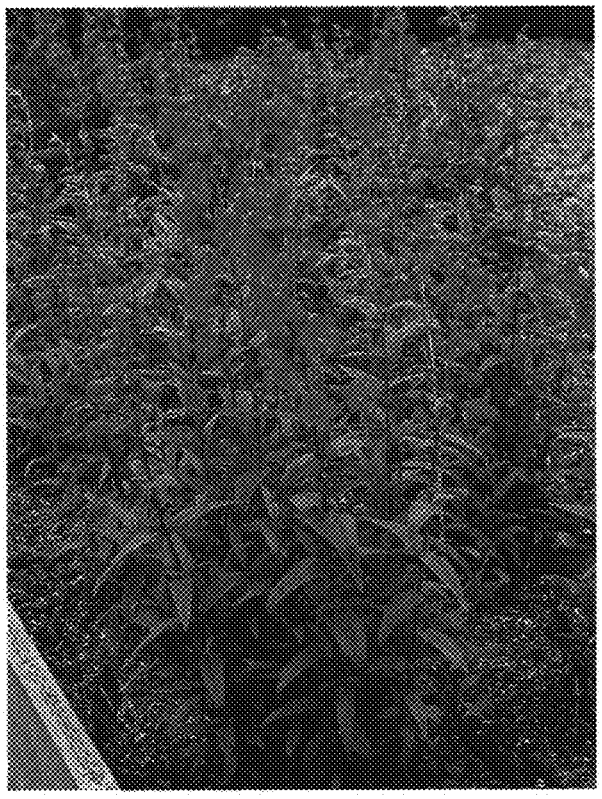
FIG. 1 on left top
FIG. 2 on left bottom